United States Patent
Fageon et al.

(10) Patent No.: US 10,105,292 B2
(45) Date of Patent: Oct. 23, 2018

(54) COMPOSITION WITH A CONTINUOUS OIL PHASE CONTAINING AT LEAST ONE LIPOPHILIC ORGANIC UV-SCREENING AGENT AND HYDROPHOBIC SILICA AEROGEL PARTICLES

(71) Applicant: L'OREAL, Paris (FR)

(72) Inventors: Laure Fageon, Paris (FR); Mathilde Lemal, Chilly-Mazarin (FR)

(73) Assignee: L'OREAL, Paris (FR)

(*) Notice: Subject to any disclaimer, the term of this patent is extended or adjusted under 35 U.S.C. 154(b) by 11 days.

(21) Appl. No.: 14/355,446

(22) PCT Filed: Oct. 25, 2012

(86) PCT No.: PCT/EP2012/071151
§ 371 (c)(1),
(2) Date: Apr. 30, 2014

(87) PCT Pub. No.: WO2013/068237
PCT Pub. Date: May 16, 2013

(65) Prior Publication Data
US 2014/0370062 A1    Dec. 18, 2014

Related U.S. Application Data

(60) Provisional application No. 61/557,484, filed on Nov. 9, 2011.

(30) Foreign Application Priority Data

Nov. 7, 2011 (FR) .................... 11 60058

(51) Int. Cl.
| | | |
|---|---|---|
| *A61K 8/02* | (2006.01) | |
| *A61Q 17/04* | (2006.01) | |
| *A61K 8/25* | (2006.01) | |
| *A61K 8/35* | (2006.01) | |
| *A61K 8/37* | (2006.01) | |
| *A61K 8/49* | (2006.01) | |
| *A61K 8/891* | (2006.01) | |
| *A61Q 1/00* | (2006.01) | |
| *A61Q 5/00* | (2006.01) | |
| *A61K 8/58* | (2006.01) | |
| *A61K 8/06* | (2006.01) | |

(52) U.S. Cl.
CPC .......... *A61K 8/0241* (2013.01); *A61K 8/0216* (2013.01); *A61K 8/0279* (2013.01); *A61K 8/06* (2013.01); *A61K 8/25* (2013.01); *A61K 8/35* (2013.01); *A61K 8/37* (2013.01); *A61K 8/496* (2013.01); *A61K 8/4966* (2013.01); *A61K 8/585* (2013.01); *A61K 8/891* (2013.01); *A61Q 1/00* (2013.01); *A61Q 5/00* (2013.01); *A61Q 17/04* (2013.01); *A61K 2800/20* (2013.01); *A61K 2800/412* (2013.01); *A61K 2800/522* (2013.01)

(58) Field of Classification Search
None
See application file for complete search history.

(56) References Cited

U.S. PATENT DOCUMENTS

| | | | | |
|---|---|---|---|---|
| 6,146,617 | A * | 11/2000 | Kurz et al. ............... | 424/59 |
| 7,204,973 | B2 * | 4/2007 | Goppel ............... | A61K 8/35 |
| | | | | 424/400 |
| 2005/0118124 | A1 * | 6/2005 | Reinhart .......... | A61K 8/64 |
| | | | | 424/63 |
| 2006/0177389 | A1 * | 8/2006 | Lott ........................ | 424/59 |
| 2009/0068255 | A1 | 3/2009 | Yu et al. | |

FOREIGN PATENT DOCUMENTS

| | | | | |
|---|---|---|---|---|
| DE | 202005014974 U1 * | 2/2007 | ......... | A61K 8/06 |
| WO | WO-2007/078062 A1 | 7/2007 | | |

OTHER PUBLICATIONS

Dow Corning. "Lucidity Anhydrous Sunscreen Gel" https://www.dowcorning.com/content/publishedlit/FORMUL_01312.pdf. Apr. 29, 2009.*
U.S. Appl. No. 14/355,425.
Product Information Sheet for Dow Corning® VM-2270, Aerogel Fine Particles, pp. 1-5, Jul. 12, 2007.

* cited by examiner

*Primary Examiner* — Mina Haghighatian
*Assistant Examiner* — Erin E Hirt
(74) *Attorney, Agent, or Firm* — Polsinelli PC

(57) ABSTRACT

The present invention relates to a composition comprising, in a cosmetically acceptable medium, at least one continuous oil phase, characterized in that the oil phase comprises a) at least one non-volatile non-cyclic silicone oil with a viscosity at 25° C. ranging from 4 to 5000 mm$^2$/s, better still from 4 to 1000 mm$^2$/s and even better still from 4 to 200 mm$^2$/s and b) at least one lipophilic organic UV-screening agent; and c) hydrophobic silica aerogel particles with a specific surface area per unit of mass (SM) ranging from 200 to 1500 m$^2$/g, preferably from 600 to 1200 m$^2$/g and better still from 600 to 800 m$^2$/g, and a size, expressed as the volume mean diameter (D[0.5]), of less than 1500 μm, preferably ranging from 1 to 30 μm, more preferentially from 5 to 25 μm, better still from 5 to 20 μm and even better still from 5 to 15 μm. The invention also relates to a cosmetic process for caring for and/or making up human keratin materials, especially bodily or facial skin or the hair, comprising at least the application to the surface of the keratin material of at least one composition as defined previously.

23 Claims, No Drawings

COMPOSITION WITH A CONTINUOUS OIL PHASE CONTAINING AT LEAST ONE LIPOPHILIC ORGANIC UV-SCREENING AGENT AND HYDROPHOBIC SILICA AEROGEL PARTICLES

CROSS REFERENCE TO RELATED APPLICATIONS

This application is a National Phase filing under 35 U.S.C. § 371 of PCT/EP2012/071151 filed on Oct. 25, 2012; and this application claims priority to Application No. 1160058 filed in France on Nov. 7, 2011, and this application claims the benefit of U.S. Provisional Application No. 61/557,484 filed on Nov. 9, 2011; the entire contents of all are hereby incorporated by reference.

The present invention relates to a composition comprising, in a cosmetically acceptable medium, at least one continuous oil phase, characterized in that the oil phase comprises
 a) at least one non-volatile non-cyclic silicone oil with a viscosity at 25° C. ranging from 4 to 5000 mm²/s, better still from 4 to 1000 mm²/s and even better still from 4 to 200 mm²/s and
 b) at least one lipophilic organic UV-screening agent; and
 c) hydrophobic silica aerogel particles with a specific surface area per unit of mass (SM) ranging from 200 to 1500 m²/g, preferably from 600 to 1200 m²/g and better still from 600 to 800 m²/g, and a size, expressed as the volume mean diameter (D[0.5]), of less than 1500 μm, preferably ranging from 1 to 30 μm, more preferentially from 5 to 25 μm, better still from 5 to 20 μm and even better still from 5 to 15 μm.

The invention also relates to a cosmetic process for caring for and/or making up human keratin materials, especially bodily or facial skin or the hair, comprising at least the application to the surface of the keratin material of at least one composition as defined previously.

It is known that light radiation with wavelengths of between 280 nm and 400 nm permits tanning of the human epidermis and that light radiation with wavelengths between 280 and 320 nm, known as UV-B rays, harm the development of a natural tan. Such exposure is also liable to induce impairment in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays bring about immediate and persistent tanning of the skin. Daily exposure to UVA rays, even for a short period, under normal conditions may lead to degradation of the collagen and elastin fibres, which is reflected by a change in the skin's microrelief, the appearance of wrinkles and non-uniform pigmentation (brown spots, or heterogeneity of the complexion).

Many photoprotective compositions have been proposed to date to overcome the effects induced by UVA and/or UVB radiation. They generally contain organic or mineral UV-screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide.

Many cosmetic compositions for photoprotecting the skin (against UV-A and/or UV-B) have been proposed to date. Formulations that are easy for the users to apply to the skin are most particularly sought. These screening cosmetic compositions must moreover satisfy the regulations in terms of protection factor and especially the European regulation on antisun products, in particular on the protection ratio between UVB and UVA and more particularly the SPF/PPD ratio, which must be less than 3.

The efficacy of antisun compositions for UV-B protection is generally expressed by the sun protection factor (SPF), which is expressed mathematically by the ratio of the dose of UV radiation necessary to reach the erythema-forming threshold with the UV-screening agent to the dose of UV radiation necessary to reach the erythema-forming threshold without UV-screening agent. This factor thus concerns the protection efficacy, the biological spectrum of action of which is centred in the UVB range, and consequently takes into account the protection with respect to this UV-B radiation.

To characterize the protection with respect to UV-A, the PPD (persistent pigment darkening) method, which measures the skin colour observed 2 to 4 hours after exposure of the skin to UV-A, is particularly recommended and used. This method has been adopted since 1996 by the Japanese Cosmetic Industry Association (JCIA) as official test procedure for the UV-A labelling of products and is frequently used by test laboratories in Europe and the United States (Japan Cosmetic Industry Association Technical Bulletin. Measurement Standards for UVA protection efficacy. Issued Nov. 21, 1995 and effective as of Jan. 1, 1996).

The $UVA_{PPD}$ sun protection factor (UVAppd PF) is expressed mathematically by the ratio of the UV-A radiation dose necessary to reach the pigmentation threshold with the UV-screening agent (MPPDp) to the UV-A radiation dose necessary to reach the pigmentation threshold without UV-screening agent (MPPDnp).

$$FP\ UVA_{PPD} = \frac{MPPD_p}{MPPD_{np}}$$

Antisun compositions are quite often in the form of an emulsion of oil-in-water type (i.e. a cosmetically acceptable support consisting of an aqueous dispersing continuous phase and of an oily dispersed discontinuous phase) or of the water-in-oil type (i.e. a cosmetically acceptable support consisting of an oily dispersing continuous phase and of an aqueous dispersed discontinuous phase) which contains, in various concentrations, one or more standard lipophilic and/or hydrophilic organic screening agents, which are capable of selectively absorbing harmful UV rays, these screening agents (and the amounts thereof) being selected as a function of the desired sun protection factor.

However, the incorporation of organic UV-screening agents into this type of cosmetic composition occasionally leads to an uncomfortable cosmetic feel, in particular a tacky effect during application to the skin, and which persists over time. These cosmetic compositions containing organic screening agents have a tendency to leave a glossy film on the surface of the skin.

The glossy effect afforded by lipophilic organic UV-screening agents is all the more substantial the greater their content in the compositions; it is therefore particularly substantial for antisun compositions with high levels of SPF and PPD protection.

Galenical forms that are anhydrous or in the form of water-in-oil emulsions or inverse emulsions are appreciated for making antisun compositions, since they offer better remanence, especially water resistance.

However, the glossy effect afforded by lipophilic organic UV-screening agents is particularly substantial in this type of galenical form, whose continuous phase is fatty.

To reduce this tacky and glossy effect of sunscreens, it has been proposed to use matting fillers such as kaolinite, silica, polymeric fillers such as PMMA fillers, and wax or silicone resin powders, for example. The introduction of these fillers into an antisun composition has a reduced effect on the glossiness of the skin at low concentration, and leads to a pilling effect once the concentration is increased. Furthermore, the feel obtained is generally dry and coarse.

Another solution known to those skilled in the art for reducing the glossy effects of antisun products is to use silicone elastomers. Such a solution is proposed in patent application WO 2007/148 293, which combines UV-screening agents with emulsifying and non-emulsifying silicone elastomers. Due to the low compatibility of sunscreens and their polar solvents with silicone elastomers, this type of composition does not allow the inclusion of high levels of screening agents and therefore does not make it possible to obtain high protection levels.

There is thus still a need for antisun compositions in anhydrous form or in inverse emulsion form, which have a high level of protection and which are matt on application, without any pilling effect or any dry/dragging effect on the skin, after application.

The Applicant has discovered, surprisingly, that this objective can be achieved by using hydrophobic silica aerogel particles in a composition with a continuous oil phase in particular in anhydrous or water/oil emulsion form comprising at least one lipophilic organic UV-screening agent and at least one non-volatile non-cyclic silicone oil.

This discovery forms the basis of the present invention.

The present invention relates to a composition comprising, in a cosmetically acceptable medium, at least one continuous oil phase, characterized in that the said oil phase comprises a) at least one non-volatile non-cyclic silicone oil with a viscosity at 25° C. ranging from 4 to 5000 $mm^2/s$, better still from 4 to 1000 $mm^2/s$ and even better still from 4 to 200 $mm^2/s$ and b) at least one lipophilic organic UV-screening agent; and c) hydrophobic silica aerogel particles with a specific surface area per unit of mass (SM) ranging from 200 to 1500 $m^2/g$, preferably from 600 to 1200 $m^2/g$ and better still from 600 to 800 $m^2/g$, and a size, expressed as the volume mean diameter (D[0.5]), of less than 1500 μm, preferably ranging from 1 to 30 μm, more preferentially from 5 to 25 μm, better still from 5 to 20 μm and even better still from 5 to 15 μm.

The invention also relates to a cosmetic process for caring for and/or making up human keratin materials, especially bodily or facial skin or the hair, comprising at least the application to the surface of the keratin material of at least one composition as defined previously.

The term "human keratin materials" means the skin (of the body, face and around the eyes), hair, eyelashes, eyebrows, bodily hair, nails, lips or mucous membranes.

The term "cosmetically acceptable medium" means any medium that is compatible with the skin and/or its integuments, which has a pleasant colour, odour and feel, and which does not cause any unacceptable discomfort (stinging, tautness or redness) liable to discourage the consumer from using this composition.

The term "lipophilic organic UV-screening agent" means an organic molecule that is capable of screening out UV radiation between 290 and 400 nm, and which can be dissolved in molecular form or dispersed in an oil phase in order to obtain a macroscopically homogeneous phase.

The term "organic molecule" means any molecule comprising in its structure one or more carbon atoms.

Hydrophobic Silica Aerogel Particles

A composition according to the invention also comprises silica aerogel particles, which are intended to stabilize the composition according to the invention by positioning themselves at the dispersed phase/continuous phase interface.

Aerogels are ultra-light porous materials, the first ones of which were made by Kristler in 1932.

They are generally synthesized via a sol-gel process in liquid medium and then dried by extraction of a supercritical fluid. The supercritical fluid most commonly used is supercritical $CO_2$. This type of drying makes it possible to avoid shrinkage of the pores and of the material.

Other types of drying also make it possible to obtain porous materials from gel, namely (i) drying by cryodesiccation, which consists in solidifying the gel at low temperature and then in subliming off the solvent, and (ii) drying by evaporation. The materials thus obtained are then known, respectively, as cryogels and xerogels. The sol-gel process and the various drying processes are described in detail in Brinker C J., and Scherer G. W., Sol-Gel Science: New York: Academic Press, 1990.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

The hydrophobic aerogel particles used in the present invention are hydrophobic silica aerogel particles with a specific surface area per unit of mass (SM) ranging from 200 to 1500 $m^2/g$, preferably from 600 to 1200 $m^2/g$ and better still from 600 to 800 $m^2/g$, and a size, expressed as the volume mean diameter (D[0.5]), of less than 1500 μm, preferably ranging from 1 to 30 μm, more preferentially from 5 to 25 μm, better still from 5 to 20 μm and even better still from 5 to 15 μm.

According to one advantageous embodiment, the hydrophobic silica aerogel particles have an oil absorption capacity, measured at the wet point, ranging from 5 to 18 ml/g, preferably from 6 to 15 ml/g and better still from 8 to 12 ml/g of particles.

The oil-absorbing capacity measured at the wet point, noted Wp, corresponds to the amount of water that needs to be added to 100 g of particle in order to obtain a homogeneous paste.

It is measured according to the "wet point" method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles used according to the present invention are preferably silylated silica aerogel particles (INCI name: silica silylate).

The preparation of hydrophobic silica aerogel particles that have been surface-modified by silylation is described more fully in U.S. Pat. No. 7,470,725.

Use will be made in particular of hydrophobic silica aerogel particles surface-modified with trimethylsilyl groups.

The hydrophobic aerogel particles that may be used in the present invention advantageously have a size, expressed as the mean diameter (D[0.5]), of less than 1500 µm, preferably ranging from 1 to 30 µm, preferably from 5 to 25 µm, better still from 5 to 20 µm and even better still from 5 to 15 µm.

The specific surface per unit of weight can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the aerogel particles according to the invention may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic aerogel particles used in the present invention have a specific surface area per unit of mass (SM) ranging from 600 to 800 m$^2$/g and a size, expressed as the volume mean diameter (D[0.5]), ranging from 5 to 20 µm and better still from 5 to 15 µm.

The hydrophobic aerogel particles used in the present invention may advantageously have a tamped density ρ ranging from 0.04 g/cm$^3$ to 0.10 g/cm$^3$ and preferably from 0.05 g/cm$^3$ to 0.08 g/cm$^3$.

In the context of the present invention, this density may be assessed according to the following protocol, known as the tamped density protocol:

40 g of powder are poured into a measuring cylinder and the cylinder is then placed on an Stay 2003 machine from Stampf Volumeter. The cylinder is then subjected to a series of 2500 tamping actions (this operation is repeated until the difference in volume between two consecutive tests is less than 2%); the final volume Vf of tamped powder is then measured directly on the cylinder.

The tamped density is determined by the ratio: mass m/Vf, in this instance 40/Vf (Vf being expressed in cm$^3$ and m in g).

According to one embodiment, the hydrophobic aerogel particles used in the present invention have a specific surface area per unit of volume SV ranging from 5 to 60 m$^2$/cm$^3$, preferably from 10 to 50 m$^2$/cm$^3$ and better still from 15 to 40 m$^2$/cm$^3$.

The specific surface per unit of volume is given by the relationship: SV=SM*ρ where ρ is the tamped density expressed in g/cm$^3$ and SM is the specific surface area per unit of mass expressed in m$^2$/g, as defined above.

Mention may be made, as hydrophobic silica aerogels which can be used in the invention, for example, of the aerogel sold under the name VM-2260 (INCI name: Silica silylate) by the company Dow Corning, the particles of which have an average size of approximately 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g.

The silica aerogel particles in accordance with the invention are preferably present in the cosmetic composition in an amount of active material ranging from 0.5% to 15% by weight and more preferentially from 1% to 10% by weight relative to the total weight of the composition.

The composition according to the invention is preferably in the form of an anhydrous composition or in the form of a water-in-oil emulsion comprising a continuous oil phase and an aqueous phase dispersed in the said oil phase.

For the purposes of the present invention, the term "anhydrous" refers to a composition comprising a content of less than or equal to 1% by weight and preferably less than or equal to 0.5% by weight of water relative to the total weight of the said composition, or is even free of water. Where appropriate, such small amounts of water may especially be introduced by ingredients of the composition that may contain residual amounts thereof.

Oily Phase

According to one particular form of the invention, the compositions in accordance with the invention may comprise at least one oil phase.

The oil phase generally comprises at least one non-volatile non-cyclic silicone oil and optionally at least one non-volatile hydrocarbon-based oil.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils, which are liquid at room temperature, having a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

In the context of the anhydrous compositions, the oil phase may be present in the composition according to the invention in an amount ranging from 50% to 99% and better still from 60% to 99% by weight relative to the total weight of the composition.

In the case of water-in-oil emulsions, the oil phase may be present in the composition according to the invention in an amount ranging from 10% to 90% and better still from 30% to 90% by weight relative to the total weight of the composition.

a) Non-Volatile Hydrocarbon-Based Oils

As non-volatile hydrocarbon-based oils that may be used according to the invention, mention may be made especially of:

hydrocarbon-based oils of plant origin such as triglyceride esters, which are generally fatty acid triesters of glycerol, the fatty acids of which may have chain lengths varying from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; or else caprylic/capric acid triglycerides, for instance those sold by the company Stéarineries Dubois or those sold under the names Miglyol 810, 812 and 818 by the company Dynamit Nobel, (ii) synthetic ethers containing from 10 to 40 carbon atoms;
(iii) linear or branched hydrocarbons of mineral or synthetic origin, such as petroleum jelly, polydecenes, hydrogenated polyisobutene such as Parleam, and squalane, and mixtures thereof;
(iv) synthetic esters, for instance the oils of formula RCOOR' in which R represents a linear or branched fatty acid residue comprising from 1 to 40 carbon atoms and R' represents a hydrocarbon-based chain that is especially branched, containing from 1 to 40 carbon atoms, on condition that R+R'≥10, for instance purcellin oil (cetostearyl octanoate), isopropyl myristate, isopropyl palmitate, $C_{12}$-$C_{15}$ alkyl benzoate, for instance the product sold under the trade name Finsolv TN or Witconol TN by the company Witco or Tegosoft TN by the company Evonik Goldschmidt, 2-ethyl phenyl benzoate, for instance the commercial product sold under the name X-Tend 226 by the company ISP, isopropyl lanolate, hexyl laurate, diisopropyl adipate, isononyl isononanoate, oleyl erucate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate, diisostearyl malate; and pentaerythritol esters; citrates or tartrates, for instance linear $C_{12}$-$C_{13}$ dialkyl tartrates, such as those sold under the name Cosmacol ETI by the company Enichem Augusta Industriale, and also linear $C_{14}$-$C_{15}$ dialkyl tartrates such as those sold under the name Cosmacol ETL by the same company; acetates;
(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;
(vi) higher fatty acids such as oleic acid, linoleic acid or linolenic acid;
(vii) carbonates such as dicaprylyl carbonate, for instance the product sold under the name Cetiol CC by the company Cognis;
(viii) fatty amides, for instance isopropyl N-lauroyl sarcosinate, for instance the product sold under the trade name Eldew SL205 from Ajinomoto; and mixtures thereof.

According to one particular embodiment, the non-volatile hydrocarbon-based oil may be chosen from liquid lipophilic organic UV-screening agents.

The term "liquid" refers to a composition that is liquid at room temperature (25° C.) and atmospheric pressure (760 mmHg).

Preferably, the non-volatile hydrocarbon-based oil(s) in accordance with the invention are present in a content ranging from 0.5% to 95% by weight and even more particularly from 5% to 40% by weight relative to the total weight of the composition.

b) Non-Volatile Non-Cyclic Silicone Oils

Preferably, the molecular weight of the non-cyclic silicone oil is between 500 and 100 000 g/mol.

The non-cyclic silicone oils have a viscosity at 25° C. ranging from 4 to 5000 mm²/s, better still from 4 to 1000 mm²/s and even better still from 4 to 200 mm²/s.

The viscosity measurement method used in the invention to characterize the silicone oils according to the invention may be the "kinematic viscosity at 25° C. raw product CID-012-01" or the "Ubbelohde viscosity at 25° C. DIN 51562-1 PVO4001".

The non-cyclic silicone oil may have a refractive index of greater than 1.3 and especially less than 1.6.

The non-cyclic silicone oils that may be used in the makeup compositions according to the present invention are represented by the general formula (I) below:

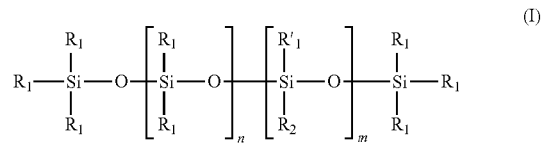

with:
$R_1$, which may be identical or different, representing:
i) a linear or branched ($C_1$-$C_{20}$) alkyl group, particularly a linear or branched $C_1$-$C_6$ group, such as methyl, ethyl, propyl or butyl; or
ii) a hydroxyl group;
$R_2$ representing:
i) a linear or branched ($C_1$-$C_{20}$)alkyl group optionally interrupted and/or terminated with a heteroatom such as O, S or N; in particular, i) is a linear or branched $C_1$-$C_6$ alkyl group, such as methyl, ethyl, propyl or butyl;
ii) a group ($C_1$-$C_9$)(poly)haloalkyl, especially perfluoroalkyl, comprising from 1 to 9 halogen atoms, particularly fluorine, such as trifluoromethyl; and
iii) the polysiloxane group —O—[Si($R_1$)$_2$—O]n'-Si($R_1$)$_3$ with $R_1$ as defined previously;
$R'_1$ representing a radical $R_1$ or $R_2$ as defined previously;
m being an integer inclusively between 0 and 150 and preferably between 20 and 100;
n and n', which may be identical or different, being an integer inclusively between 1 and 300 and preferably between 1 and 100.

According to one preferred embodiment, $R'_1$ represents a radical $R_1$, and more particularly a group ($C_1$-$C_6$)alkyl such as methyl.

According to one particular embodiment, m is 0.

According to another particular embodiment of the invention, $R_1$ is a methyl, and more particularly m is 0 and $R_1$ is a methyl.

According to one particular example of the invention, the non-cyclic silicone oils may be chosen from a fluorosilicone compound.

Fluorosilicone compounds that may especially be mentioned include those sold by the company Shin-Etsu under the names X22-819, X22-820, X22-821 and X22-822 or FL-100.

According to one preferred embodiment, the said non-cyclic silicone oil is a dimethicone corresponding to formula (II) below:

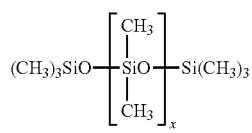 (II)

in this formula (II), x being an integer ranging from 1 to 50, better still from 1 to 20 and more specifically from 1 to 10. The molecular mass of such a compound may be, for example, approximately 770 g/mol. Preferably, x is equal to 8.

According to one particular embodiment, the non-cyclic silicone oil of general formula (I) or (II) is advantageously chosen from the oils sold by the company Dow Corning under the reference 200R Fluid 5 cSt® and under the references 200R Fluid 100 cSt®, Dow Corning 200 Fluid 350 cSt and Dow Corning 200 Fluid 200-350 cSt®.

Preferably, the non-cyclic silicone oil in accordance with the invention is present in a content ranging from 5% to 95% by weight and particularly from 5% to 60% by weight relative to the total weight of the composition.

c) Volatile Oils

The oil phase of the compositions according to the invention may also contain at least one volatile hydrocarbon-based oil and/or at least one volatile silicone oil.

Volatile silicone oils that may be mentioned, for example, include volatile linear or cyclic silicone oils, especially those with a viscosity ≤8 centistokes ($8\times10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As volatile hydrocarbon-based oils that may be used according to the invention, mention may be made especially of hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane, and the alkanes described in the patent applications from the company Cognis WO 2007/068 371 or WO 2008/155 059 (mixtures of different alkanes differing by at least one carbon). These alkanes are obtained from fatty alcohols, which are themselves obtained from coconut oil or palm oil, the oils sold under the trade name Isopar or Permethyl, branched $C_8$-$C_{16}$ esters isohexyl neopentanoate, and mixtures thereof.

Other volatile hydrocarbon-based oils, for instance petroleum distillates, especially those sold under the name Shell Solt by the company Shell, may also be used. According to one embodiment, the volatile solvent is chosen from volatile hydrocarbon-based oils containing from 8 to 16 carbon atoms, and mixtures thereof.

Lipophilic Organic Screening Agents

The lipophilic organic UV-screening agents are chosen especially from cinnamic derivatives; anthranilates; salicylic derivatives; dibenzoylmethane derivatives, camphor derivatives; benzophenone derivatives; β,β-diphenylacrylate derivatives; triazine derivatives; benzotriazole derivatives; benzalmalonate derivatives, especially those mentioned in U.S. Pat. No. 5,624,663; imidazolines; p-aminobenzoic acid (PABA) derivatives; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives such as those described in patent applications WO 04/006 878, WO 05/058 269, WO 06/032 741, FR 2 957 249 and FR 2 957 250; and mixtures thereof.

As examples of additional organic photoprotective agents, mention may be made of those denoted hereinbelow under their INCI name:

As examples of lipophilic organic UV-screening agents, mention may be made of those denoted hereinbelow under their INCI name:

Dibenzoylmethane Derivative:
Butylmethoxydibenzoylmethane or avobenzone sold under the trade name Parsol 1789 by the company DSM Nutritional Products,
Para-Aminobenzoic Acid Derivatives:
PABA,
Ethyl PABA,
Ethyl Dihydroxypropyl PABA,
Ethylhexyl Dimethyl PABA sold in particular under the name Escalol 507 by ISP,
Salicylic Derivatives:
Homosalate sold under the name Eusolex HMS by Rona/EM Industries,
Ethylhexyl salicylate sold under the name Neo Heliopan OS by Symrise,
Cinnamic Derivatives:
Ethylhexyl methoxycinnamate sold especially under the trade name Parsol MCX by DSM Nutritional Products,
Isopropyl methoxycinnamate,
Isoamyl methoxycinnamate sold under the trade name Neo Heliopan E 1000 by Symrise, Cinoxate,
Diisopropyl methylcinnamate,
β,β-Diphenylacrylate Derivatives:
Octocrylene sold especially under the trade name Uvinul N539 by BASF,
Etocrylene sold in particular under the trade name Uvinul N35 by BASF,
Benzophenone Derivatives:
Benzophenone-1 sold under the trade name Uvinul 400 by BASF,
Benzophenone-2 sold under the trade name Uvinul D50 by BASF,
Benzophenone-3 or oxybenzone sold under the trade name Uvinul M40 by BASF,
Benzophenone-6 sold under the trade name Helisorb 11 by Norquay, Benzophenone-8 sold under the trade name Spectra-Sorb UV-24 by American Cyanamid,
Benzophenone-12,
N-hexyl 2-(4-diethylamino-2-hydroxybenzoyl)benzoate sold under the trade name Uvinul A+ or in the form of a mixture with octyl methoxycinnamate under the trade name Uvinul A+B by BASF,
1,1'-(1,4-piperazinediyl)bis[1-[2-[4-(diethylamino)-2-hydroxybenzoyl]phenyl]methanone (CAS 919803-06-8) in micronized or non-micronized form,
Benzylidenecamphor Derivatives:
3-Benzylidene Camphor manufactured under the name Mexoryl SD by Chimex,
4-Methylbenzylidene Camphor sold under the name Eusolex 6300 by Merck,
Polyacrylamidomethylbenzylidenecamphor manufactured under the name Mexoryl SW by Chimex,
Phenylbenzotriazole Derivatives:
Drometrizole trisiloxane sold under the name Silatrizole by Rhodia Chimie,
Triazine Derivatives:
bis-Ethylhexyloxyphenol methoxyphenyl triazine sold under the trade name Tinosorb S by BASF,
Ethylhexyl triazone sold in particular under the trade name Uvinul T150 by BASF,
Diethylhexyl Butamido Triazone sold under the trade name Uvasorb HEB by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
Anthranilic Derivatives:
Menthyl Anthranilate sold under the trade name Neo Heliopan MA by Symrise,
Imidazoline Derivatives:
Ethylhexyl dimethoxybenzylidene dioxoimidazoline propionate,
Benzalmalonate Derivatives:
Dineopentyl 4'-methoxybenzalmalonate,
Polyorganosiloxane containing benzalmalonate functions, for instance Polysilicone-15, sold under the trade name Parsol SLX by DSM,
4,4-Diarylbutadiene Derivatives:
1,1-dicarboxy(2,2'-dimethylpropyl)-4,4-diphenylbutadiene.
Benzoxazole Derivatives:
2,4-Bis[4-[5-(1,1-dimethylpropyl)benzoxazol-2-yl]phenylimino]-6-[(2-ethylhexyl)imino]-1,3,5-triazine, sold under the name of Uvasorb K2A by Sigma 3V,
and mixtures thereof.
Lipophilic Merocyanin Derivatives:
Octyl 5-N,N-diethylamino-2-phenylsulfonyl-2,4-pentadienoate
and mixtures thereof.
The preferential liposoluble or insoluble organic screening agents are chosen from:
Butylmethoxydibenzoylmethane
Ethylhexyl methoxycinnamate,
Ethylhexyl salicylate,
Homosalate,
Butylmethoxydibenzoylmethane,
Octocrylene,
Benzophenone-3,
n-Hexyl 2-(4-diethylamino-2-hydroxybenzoyl)benzoate,
4-Methylbenzylidenecamphor,
Bis(ethylhexyloxyphenyl)methoxyphenyltriazine,
Ethylhexyl triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole Trisiloxane,
Polysilicone-15,
1,1-dicarboxy(2,2'-dimethylpropyl)-4,4-diphenylbutadiene,
2,4-Bis[4-[5-(1,1-dimethylpropyl)benzoxazol-2-yl]phenylimino]-6-[(2-ethylhexyl)imino]-1,3,5-triazine,
and mixtures thereof.

The preferential lipophilic organic screening agents are chosen from:
Butylmethoxydibenzoylmethane,
Octocrylene,
Ethylhexyl salicylate,
n-Hexyl 2-(4-diethylamino-2-hydroxybenzoyl)benzoate,
Bis(ethylhexyloxyphenyl)methoxyphenyltriazine,
Ethylhexyl triazone,
Diethylhexyl Butamido Triazone,
Drometrizole trisiloxane, and mixtures thereof.

The lipophilic organic UV-screening agent(s) are preferably present in the compositions according to the invention in a content ranging from 0.1% to 40% by weight and in particular from 5% to 25% by weight relative to the total weight of the composition.

Water-in-Oil Emulsion

The aqueous phase may be present in the composition according to the invention in an amount ranging from 0.1% to 50% and better still from 5% to 30% by weight relative to the total weight of the composition.

The emulsification processes that may be used are of the paddle or propeller, rotor-stator and HPH type.

It is also possible, via HPH (between 50 and 800 bar), to obtain stable dispersions with drop sizes that may be as low as 100 nm.

The emulsions generally contain at least one emulsifying surfactant chosen from amphoteric, anionic, cationic and nonionic emulsifying surfactants, which are used alone or as a mixture.

The emulsifiers are chosen so as to obtain a water-in-oil emulsion.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyl-dimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE O9 by the company Goldschmidt. One or more coemulsifiers may also be added thereto, which may be chosen advantageously from the group consisting of polyol alkyl esters.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers; and mixtures thereof.

The composition according to the invention may comprise a polyol that is miscible with water at room temperature. Such polyols may promote the moisturization of the surface of the skin on which the composition is applied.

In addition, the composition according to the invention may comprise a monoalcohol containing from 2 to 6 carbon atoms, such as ethanol or isopropanol.

Adjuvants

The compositions in accordance with the present invention may also comprise one or more standard cosmetic adjuvants chosen from oils, waxes, organic solvents, hydrophilic UV-screening agents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, colouring agents, polymers, propellants, acidifying or basifying agents or any other ingredient usually used in cosmetics and/or dermatology.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

Mention may be made, among organic solvents, for example, of lower alcohols and polyols. These polyols may be chosen from glycols and glycol ethers, for instance ethylene glycol, propylene glycol, butylene glycol, dipropylene glycol or diethylene glycol.

According to one particular form of the invention, the compositions according to the invention may also comprise insoluble UV-screening agents chosen from insoluble organic and inorganic UV-screening agents and composite materials comprising an organic or inorganic matrix and at least one inorganic UV-screening agent.

Insoluble Screening Agents

The term "insoluble UV-screening agent" means any UV-screening agent that may be in the form of particles in a liquid fatty phase and in a liquid aqueous phase.

The insoluble organic UV-screening agent(s) are preferably present in the compositions according to the invention in a content ranging from 0.1% to 10% by weight and in particular from 0.5% to 5% by weight relative to the total weight of the composition.

Insoluble Organic UV-Screening Agents

Among the organic insoluble screening agents, mention may be made of those described in patent applications U.S. Pat. No. 5,237,071, U.S. Pat. No. 5,166,355, GB 2 303 549, DE 197 26 184 and EP 893 119, especially methylenebis (hydroxyphenylbenzotriazole) derivatives such as methylenebis(benzotriazolyl)tetramethylbutylphenol sold in solid form under the trade name Mixxim BB/100 by Fairmount Chemical or in micronized form in aqueous dispersion under the trade name Tinosorb M by BASF.

Mention may also be made of the symmetrical triazine screening agents described in patent U.S. Pat. No. 6,225,467, patent application WO 2004/085412 (see compounds 6 and 9) or the document "Symmetrical Triazine Derivatives" IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl)-1,3,5-triazine) and 2,4,6-tris(terphenyl)-1,3,5-triazine which is also mentioned in Beiersdorf patent applications WO 06/035 000, WO 06/034 982, WO 06/034 991, WO 06/035 007, WO 2006/034 992 and WO 2006/034 985.

Inorganic UV-Screening Agents

The inorganic UV-screening agents used in accordance with the present invention are metal oxide pigments.

More preferentially, the inorganic UV-screening agents of the invention are metal oxide pigments with a mean elemental particle size of less than or equal to 0.5 μm, more preferentially between 0.005 μm and 0.5 μm and even more preferentially between 0.001 μm and 0.1 μm, and preferentially between 0.015 μm and 0.05 μm.

The term "mean size" of the particles is understood to mean the parameter D[4.3] measured using a "Mastersizer 2000" particle size analyser (Malvern). The light intensity scattered by the particles as a function of the angle at which they are lit is converted to size distribution according to Mie theory. The parameter D[4.3] is measured; this is the mean diameter of the sphere having the same volume as the particle. For a spherical particle, reference will often be made to the "mean diameter".

The expression "mean elementary size" is understood to mean the size of non-aggregated particles.

They may be chosen especially from titanium oxide, zinc oxide, iron oxide, zirconium oxide and cerium oxide, or mixtures thereof, and more particularly titanium oxides.

Such coated or uncoated metal oxide pigments are described in particular in patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
  with silica, such as the product Sunveil from the company Ikeda,
  with silica and iron oxide, such as the product Sunveil F from the company Ikeda,
  with silica and alumina, such as the products Microtitanium Dioxide MT 500 SA and Microtitanium Dioxide MT 100 SA from the company Tayca and Tioveil from the company Tioxide,
  with alumina, such as the products Tipaque TTO-55 (B) and Tipaque TTO-55 (A) from the company Ishihara and UVT 14/4 from the company Kemira,
  with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF $TiO_2SI_3$ by the company Cardre, anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wacker under the name Transparent titanium oxide PW, by the company Miyoshi Kasei under the name UFTR, by the company Tomen under the name ITS and by the company Tioxide under the name Tioveil AQ.

The uncoated zinc oxide pigments are for example:
those sold under the name Z-Cote by the company Sunsmart;
those sold under the name Nanox by the company Elementis;
those sold under the name Nanogard WCD 2025 by the company Nanophase Technologies.

The coated zinc oxide pigments are for example:
those sold under the name Zinc Oxide CS-5 by the company Toshibi (ZnO coated with polymethylhydrogenosiloxane);
those sold under the name Nanogard Zinc Oxide FN by the company Nanophase Technologies (as a 40% dispersion in Finsolv TN, $C_{12}$-$C_{15}$ alkyl benzoate);
those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name NFD Ultrafine ZnO by the company Daikin (ZnO coated with perfluoroalkyl phosphate and copolymer based on perfluoroalkylethylacrylate as a dispersion in cyclopentasiloxane);
those sold under the name SPD-Z1 by the company Shin-Etsu (ZnO coated with silicone-grafted acrylic polymer, dispersed in cyclodimethylsiloxane);
those sold under the name Escalol Z100 by the company ISP (alumina-treated ZnO dispersed in an ethylhexyl methoxycinnamate/PVP-hexadecene/methicone copolymer mixture);
those sold under the name Fuji ZnO-SMS-10 by the company Fuji Pigment (ZnO coated with silica and polymethylsilsesquioxane);
those sold under the name Nanox Gel TN by the company Elementis (ZnO dispersed at a concentration of 55% in C12-C15 alkyl benzoate with hydroxystearic acid polycondensate).

The uncoated cerium oxide pigments are sold under the name Colloidal Cerium Oxide by the company Rhône-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

According to the invention, coated or uncoated titanium oxide pigments are particularly preferred.

According to one particular form of the invention, the insoluble screening agents may consist of composite particles with a mean size of between 0.1 and 30 μm comprising a matrix and an inorganic UV-screening agent, the content of inorganic screening agent in a particle ranging from 1% to 70% by weight, These composite particles may be chosen from composite spherical particles and composite lamellar particles, or mixtures thereof.

The term "spherical" means that the particle has a sphericity index, i.e. the ratio between its largest diameter and its smallest diameter, of less than 1.2.

The term "non-spherical" refers to particles in three dimensions (length, width and thickness or height) for which the ratio of the longest dimension to the shortest dimension is greater than 1.2. The dimensions of the particles of the invention are evaluated by scanning electron microscopy and image analysis. They include particles of parallelepipedal shape (rectangular or square surface area), discoid shape (circular surface area) or ellipsoid shape (oval surface area), characterized by three dimensions: a length, a width and a height. When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width may be of identical or different dimensions: when they are of the same dimension, the shape of the surface of the parallelepiped is a square; in the contrary case, the shape is rectangular. As regards the height, it corresponds to the thickness of the parallelepiped.

The spherical and non-spherical screening composite particles used according to the present invention comprise a matrix and an inorganic UV-screening agent. The matrix comprises one or more organic and/or inorganic materials.

The inorganic UV-screening agent is generally chosen from metal oxides, preferably titanium, zinc or iron oxides or mixtures thereof and more particularly from titanium dioxide $TiO_2$.

These metal oxides may be in the form of particles with a mean size generally of less than 0.2 μm. Advantageously, the metal oxide particles used have a mean elementary size of less than or equal to 0.1 μm.

These metal oxides may also be in the form of layers, preferably multilayers with a mean thickness generally of less than 0.2 μm.

According to a first variant, the composite particles contain a matrix comprising an organic and/or inorganic material, in which matrix particles of inorganic UV-screening agent are included. According to this embodiment, the matrix has inclusions and particles of inorganic UV screening agent are placed in the inclusions of the matrix.

According to a second variant, the composite particles contain a matrix made of an organic and/or inorganic material, which matrix is covered with at least one layer of inorganic UV screening agent which may be connected to the matrix with the aid of a binder.

According to a third variant, the composite particles contain an inorganic UV screening agent covered with at least one layer of an organic and/or inorganic material.

The matrix may also be formed from one or more organic or inorganic materials. It may then be a continuous phase of materials such as an alloy, i.e. a continuous phase in which the materials can no longer be dissociated, or a discontinuous phase of materials, for example constituted of an organic or inorganic material covered with a layer of another different organic or inorganic material.

According to one variant, in particular when the spherical composite particles comprise a matrix covered with a layer of UV-screening agent, the composite particles may furthermore be covered with an additional coating, in particular chosen from biodegradable or biocompatible materials, lipid materials, for instance surfactants or emulsifiers, polymers, and oxides.

Spherical Composite Particles

The inorganic materials that may be used in the matrix of the spherical composite particles according to the present invention may be chosen from the group formed by boron nitride, glass, calcium carbonate, barium sulfate, hydroxyapatite, silica, silicate, magnesium sulfate, magnesium carbonate, aluminium oxide, calcium silicate, calcium phosphate, magnesium oxide and bismuth oxychloride, and mixtures thereof.

The organic materials that may be used to form the matrix are chosen from the group formed by poly(meth)acrylates, polyamides, silicones, polyurethanes, polyethylenes, polypropylenes, polystyrenes, polyhydroxyalkanoates, polycaprolactams, poly(butylene)succinates, polysaccharides, polypeptides, polyvinyl alcohols, polyvinyl resins, fluoropolymers, waxes, polyesters, polyethers, and mixtures thereof.

Preferably, the matrix of the spherical composite particle contains a material or mixture of materials chosen from:
$SiO_2$,
polymethyl methacrylate,
copolymers of styrene and of a C1/C5 alkyl (meth) acrylate derivative,
polyamides, such as nylon.

The composite particles in spherical form are characterized by a mean diameter of between 0.1 μm and 30 μm, preferably between 0.3 μm and 20 μm and even more preferably between 0.5 μm and 10 μm.

According to a first variant, the spherical composite particles contain a matrix comprising an organic and/or inorganic material, in which matrix particles of inorganic UV-screening agent are included.

According to this first variant, the particles of inorganic UV-screening agent are characterized by a mean elementary size generally of less than 0.2 μm. Advantageously, the metal oxide particles used have a mean elementary size of less than or equal to 0.1 μm.

As composite particles corresponding to this variant, mention may be made of the products Sunsil TIN 50 and Sunsil TIN 40 sold by the company Sunjin Chemical. These spherical composite particles having a mean size between 2 and 7 μm are formed of $TiO_2$ encapsulated in a silica matrix.

Mention may also be made of the following particles:
spherical composite particles having a mean size between 4 and 8 μm, containing $TiO_2$ and $SiO_2$ and having the trade name Eospoly TR sold by the company Creations Couleurs,
composite particles containing $TiO_2$ and a styrene/alkyl acrylate copolymer matrix sold under the name Eospoly UV TR22 HB 50 by the company Creations Couleurs,
composite particles containing $TiO_2$ and ZnO and a PMMA matrix and having the trade name Sun PMMA-T50 sold by the company Sunjin Chemical.

According to a second variant, the spherical composite particles contain a matrix made of an organic and/or inorganic material, covered with at least one layer of inorganic UV-screening agent connected to the matrix by means of a binder.

According to this second variant, the mean thickness of the layer of inorganic UV-screening agent is generally about ten nanometers. The mean thickness of the layer of inorganic UV screening agent is advantageously between $10^{-3}$ and 0.2 μm and preferably between 0.001 and 0.2 μm.

The spherical composite particles used according to the invention have a size of between 0.1 and 0.3 μm, preferably between 0.3 and 20 μm and even more preferentially between 0.5 and 10 μm.

Among the composite particles that can be used according to the invention, mention is made of spherical composite particles containing $TiO_2$ and $SiO_2$ and having the trade name STM ACS-0050510, supplied by the company JGC Catalysts and Chemical.

According to a third variant, the spherical composite particles contain an inorganic UV-screening agent covered with at least one layer of an organic and/or inorganic material. According to this third variant, the particles of inorganic UV screening agent are characterized by a mean elementary size generally of between $10^{-3}$ and 200 nm. Advantageously, the metal oxide particles used have a mean elementary size between 10 nm and 100 nm.

The spherical composite particles used according to the invention have a size of between 0.1 and 30 µm, preferably between 0.3 and 20 µm and even more preferentially between 0.5 and 10 µm.

Non-Spherical Composite Particles

The organic materials that may be used to form the matrix of the screening non-spherical particles are chosen from the group formed by poly(meth)acrylates, polyamides, silicones, polyurethanes, polyethylenes, polypropylenes, polystyrenes, polyhydroxyalkanoates, polycaprolactams, poly(butylene)succinates, polysaccharides, polypeptides, polyvinyl alcohols, polyvinyl resins, fluoropolymers, waxes, polyesters, polyethers, and mixtures thereof.

Preferably, the organic materials that can be used are:
triethoxycaprylylsilane,
acrylic polymers such as polymethyl methacrylate and acrylic copolymers comprising other types of monomers such as styrene;
polyamides, such as nylon.

The inorganic materials that can be used in the matrix of the non-spherical composite particles are chosen from the group formed by mica, synthetic mica, talc, sericite, boron nitride, glass, calcium carbonate, barium sulfate, hydroxyapatite, silica, silicate, magnesium sulfate, magnesium carbonate, magnesium trisilicate, aluminium oxide, calcium silicate, calcium phosphate, magnesium oxide and bismuth oxychloride, and mixtures thereof. Preferably, these inorganic materials are chosen from:
silica,
talc;
mica;
alumina.

The inorganic UV-screening agent is generally chosen from metal oxides, in particular from titanium, zinc or iron oxides and more particularly titanium dioxide ($TiO_2$).

The non-spherical composite particles of the invention are characterized by three dimensions, of which:
the smallest is greater than 0.1 µm, preferably greater than 0.3 µm and better still greater than 0.5 µm;
the largest is less than 30 micrometers, preferably 20 micrometers and better still 10 micrometers.

The ratio of the largest to the smallest dimension is greater than 1.2.

The dimensions of the particles of the invention are evaluated by scanning electron microscopy and image analysis.

The non-spherical composite particles that may be used according to the invention will preferably be platelet-shaped.

The term "platelet-shaped" is understood to mean a parallelepipedal shape.

They may be smooth, rough or porous.

The platelet-shaped composite particles preferably have a mean thickness of between 0.01 and 10 µm, the mean length is generally between 0.5 and 30 µm and the mean width is between 0.5 and 30 µm.

The thickness is the smallest of the dimensions, the width is the medium dimension, and the length is the longest of the dimensions.

According to a first variant, the composite particles contain a matrix comprising an organic and/or inorganic material, in which matrix particles of inorganic UV-screening agent are included.

According to this first variant, the particles of inorganic UV-screening agent are characterized by a mean elementary size generally of less than 0.2 µm. Advantageously, the metal oxide particles used have a mean elementary size of less than or equal to 0.1 µm.

According to a second variant, the composite particles contain a matrix made of an organic and/or inorganic material, which matrix is covered with at least one layer of inorganic UV-screening agent which may be connected to the matrix by means of a binder.

According to this second variant, the mean thickness of the layer of inorganic UV-screening agent is generally about ten nanometers. The mean thickness of the layer of inorganic UV-screening agent is advantageously between $10^{-3}$ and 0.2 µm and preferably between 0.01 and 0.2 µm.

The non-spherical composite particles used according to the invention have a size of between 100 nm and 30 µm, preferably between 0.3 and 20 µm and even more preferentially between 0.5 and 10 µm.

According to a third variant, the non-spherical composite particles contain an inorganic UV-screening agent covered with at least one layer of an organic and/or inorganic material. According to this third variant, the particles of inorganic UV screening agent are characterized by a mean elementary size generally of between $10^{-3}$ and 0.2 µm. Advantageously, the metal oxide particles used have a mean elementary size of between 0.01 and 0.1 µm.

Preferably, the inorganic UV-screening agent used in the composite particle is chosen from metal oxides, in particular from titanium, zinc or iron oxides and more particularly titanium dioxide ($TiO_2$).

Preferably, the matrix of the composite particle contains a material or mixture of materials chosen from:
$SiO_2$,
alumina;
mica;
alumina/triethoxycaprylylsilane mixture;
talc;
PMMA (polymethyl methacrylate),
Nylon.

More preferably, the matrix of the composite particle is formed from a material or mixture of materials chosen from:
alumina,
alumina/triethoxycaprylylsilane mixture;
talc;
silica,
mica.

Among the composite particles that may be used according to the invention, mention may also be made of the following particles:
composite particles containing $TiO_2$ and an alumina matrix, of trade name Matlake OPA sold by the company Sensient LCW,
composite particles containing $TiO_2$ and an alumina/triethoxycaprylylsilane matrix, of trade name Matlake OPA AS sold by the company Sensient LCW,
composite particles containing ultrafine $TiO_2$ particles deposited on the surface of talc platelets, of trade name TTC 30 sold by the company Miyoshi Kasei,
composite particles containing ultrafine $TiO_2$ particles deposited on the surface of talc platelets, of trade name Silseem Mistypearl Yellow sold by the company Nihon Koken Kogyo (NKK).

The inorganic UV-screening agent(s) are preferably present in the compositions according to the invention in an active material content ranging from 0.1% to 20% by weight and in particular from 0.5% to 15% by weight relative to the total weight of the composition.

Hydrophilic UV-Screening Agents

The compositions in accordance with the invention in the form of a water-in-oil emulsion may comprise in the aqueous phase other hydrophilic UVA and/or UVB organic UV-screening agents.

The term "hydrophilic organic UV-screening agent" means an organic molecule that is capable of screening out UV radiation between 290 and 400 nm, and which can be dissolved in molecular form or dispersed in an aqueous phase in order to obtain a macroscopically homogeneous phase.

Among the hydrophilic UVA UV-screening agents that are capable of absorbing UV from 320 to 400 nm, mention may be made of:
  Terephthalylidenedicamphorsulfonic acid manufactured under the name Mexoryl SX by Chimex,
  Bis-benzazolyl derivatives as described in patents EP 669 323, and U.S. Pat. No. 2,463,264 and more particularly the compound disodium phenyldibenzimidazotetrasulfonate sold under the trade name Neo Heliopan AP by Haarmann & Reimer.

Among the hydrophilic UVB UV-screening agents that are capable of absorbing UV from 280 to 320 nm, mention may be made of:
  p-aminobenzoic acid (PABA) derivatives such as
    PABA,
    Glyceryl PABA, and
    PEG-25 PABA sold under the name Uvinul P25 by BASF,
  Phenylbenzimidazolesulfonic acid sold in particular under the trade name Eusolex 232 by Merck,
  ferulic acid,
  p-methoxycinnamic acid,
  DEA methoxycinnamate,
  benzylidenecamphorsulfonic acid manufactured under the name Mexoryl SL by Chimex,
  camphorbenzalkonium methosulfate manufactured under the name Mexoryl SO by Chimex.

Among the hydrophilic UVA and UVB UV-screening agents, mention may be made of:
  Benzophenone-4 sold under the trade name Uvinul MS40 by BASF,
  Benzophenone-5, and
  Benzophenone-9.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of formula (VI) below:

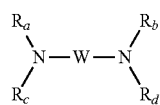
(VI)

in which W is a propylene residue optionally substituted with a hydroxyl group or a $C_1$-$C_4$ alkyl radical; and $R_a$, $R_b$, $R_c$, and $R_d$, which may be identical or different, represent a hydrogen atom or a $C_1$-$C_4$ alkyl or $C_1$-$C_4$ hydroxyalkyl radical.

Preferably, the cosmetic composition comprises one or more basifying agents selected from alkanolamines, in particular triethanolamine, and sodium hydroxide.

The pH of the composition in accordance with the invention in the form of a water-in-oil emulsion is generally between about 3 and 12, preferably between about 5 and 11 and even more particularly from 6 to 8.5.

The cosmetic compositions according to the invention find their application in a large number of treatments, especially cosmetic treatments, for the skin, the lips and the hair, including the scalp.

Another subject of the present invention consists of the use of the compositions according to the invention as defined above for the manufacture of products for the cosmetic treatment of the skin, the lips, the nails, the hair, the eyelashes, the eyebrows and/or the scalp, especially care products, antisun products and makeup products.

The cosmetic compositions according to the invention may be used, for example, as makeup products.

The cosmetic compositions according to the invention may be used, for example, as care products and/or antisun protection products for the face and/or the body, of liquid to semi-liquid consistency, such as oils, milks, more or less rich creams, cream-gels and pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in patents U.S. Pat. No. 4,077,441 and U.S. Pat. No. 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight, relative to the total weight of the composition.

Needless to say, a person skilled in the art will take care to select the abovementioned optional additional compound(s) and/or the amounts thereof such that the advantageous properties intrinsically associated with the compositions in accordance with the invention are not, or are not substantially, adversely affected by the envisaged addition(s).

A person skilled in the art will choose the said active principle or principles according to the effect desired on the skin, hair, eyelashes, eyebrows or nails.

Fillers

The compositions according to the invention may comprise, besides the hydrophobic silica aerogel particles, additional fillers.

The term "fillers" should be understood as meaning colourless or white, mineral or synthetic particles of any shape, which are insoluble and dispersed in the medium of the composition irrespective of the temperature at which the composition is manufactured.

They are mineral or organic in nature and make it possible to confer softness and mattness on the composition and a uniform makeup result on the skin.

The additional fillers used in the compositions according to the present invention may be in lamellar (or platelet), spherical (or globular) form, in the form of fibres or in any other form intermediate between these defined forms.

In the present patent application, the term "spherical particles" means particles in the form or substantially in the form of a sphere, which are insoluble in the medium of the composition according to the invention, even at the melting point of the medium (about 100° C.).

The term "lamellar particles" means herein particles of parallelepipedal shape (rectangular or square surface), discoid shape (circular surface) or ellipsoid shape (oval surface), characterized by three dimensions: a length, a width and a height, these particles being insoluble in the medium of the composition according to the invention, even at the melting point of the medium (about 100° C.).

These additional fillers may or may not be surface-coated, and in particular they may be surface-treated with silicones, amino acids, fluoro derivatives or any other substance that promotes the dispersion and compatibility of the filler in the compositions.

Among the solid mineral particles that may be used in the invention, mention may be made of talc, mica, silica, precipitated calcium carbonate, magnesium carbonate, magnesium hydrogen carbonate, hydroxyapatite and boron nitride, and mixtures thereof.

Among the solid organic particles that may be used in the invention, mention may be made of polyamide powders (Nylon® Orgasol from Atochem), poly-β-alanine powder and polyethylene powder, polytetrafluoroethylene powders (Teflon®), lauroyllysine, starch, tetrafluoroethylene polymer powders, hollow polymer microspheres such as Expancel (Nobel Industrie), metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate, Polypore® L 200 (Chemdal Corporation), silicone resin microbeads (for example Tospearl® from Toshiba), polyurethane powders, in particular powders of crosslinked polyurethane comprising a copolymer, the said copolymer comprising trimethylol hexyllactone. It may in particular be a hexamethylene diisocyanate/trimethylol hexyllactone polymer. Such particles are especially commercially available, for example, under the name Plastic Powder D-400® or Plastic Powder D-800® from the company Toshiki, and mixtures thereof.

Preferably, the additional fillers that are suitable for use in the invention may be mineral particles such as silica, mica, talc or synthetic polymers such as Nylon, acrylic polymers, polyethylene, PTFE, PMMA, starch or silicones, and mixtures thereof.

A composition according to the invention may comprise a content of filler, besides the silica aerogel, ranging from 0 to 30% by weight relative to the total weight of the composition, preferably ranging from 0.5% to 20% by weight and preferentially ranging from 1% to 10% by weight, relative to the total weight of the composition.

Colouring Agent(s)

The compositions according to the invention may also contain colouring agents.

The colouring agent(s) or dyestuffs according to the invention are preferably chosen from pigments, nacres, water-soluble or liposoluble dyes and agents for promoting the naturally pinkish colouration of the skin, and mixtures thereof.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof: cochineal carmine, organic pigments of azo dyes, anthraquinone dyes, indigoid dyes, xanthene dyes, pyrene dyes, quinoline dyes, triphenylmethane dyes and fluoran dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention may comprise a content of pigments ranging from 0 to 30% by weight relative to the total weight of the composition, preferably ranging from 2% to 20% by weight and preferentially ranging from 4% to 10% by weight, relative to the total weight of the composition.

Nacres

The term "nacres" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

The compositions according to the invention may have a nacre content ranging from 0 to 30% by weight, for example from 0.01% to 5% by weight relative to the total weight of the composition.

Besides the fillers and pigments, the particulate phase of the invention may comprise water-soluble or liposoluble dyes.

The term "liposoluble dyes" should be understood as meaning compounds that are generally organic, which are soluble in fatty substances such as oils.

The liposoluble dyes are, for example, Sudan red, D&C Red No. 17, D&C Green No. 6, β-carotene, soybean oil, Sudan Brown, D&C Yellow No. 11, D&C Violet No. 2, D&C Orange No. 5, quinoline yellow, annatto and bromo acids.

For the purposes of the invention, the term "water-soluble dye" means any natural or synthetic, generally organic compound, which is soluble in an aqueous phase or in water-miscible solvents and which is capable of colouring.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

Water-Soluble or Liposoluble Dyes

The term "liposoluble dyes" should be understood as meaning compounds that are generally organic, which are soluble in fatty substances such as oils.

The liposoluble dyes are, for example, Sudan red, D&C Red No. 17, D&C Green No. 6, β-carotene, soybean oil, Sudan Brown, D&C Yellow No. 11, D&C Violet No. 2, D&C Orange No. 5, quinoline yellow, annatto and bromo acids.

For the purposes of the invention, the term "water-soluble dye" means any natural or synthetic, generally organic compound, which is soluble in an aqueous phase or in water-miscible solvents and which is capable of colouring.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

Agents for Promoting the Naturally Pinkish Colouration of the Skin

Mention may be made especially of:
a self-tanning agent, i.e. an agent which, when applied to the skin, especially to the face, can produce a tan effect that is more or less similar in appearance to that which may result from prolonged exposure to the sun (natural tan) or under a UV lamp;
an additional colouring agent, i.e. any compound that has particular affinity for the skin, which allows it to give the skin a lasting, non-covering colouration (i.e. that does not have a tendency to opacify the skin) and that is not removed either with water or using a solvent, and that withstands both rubbing and washing with a solution containing surfactants. Such a lasting colouration is thus distinguished from the superficial and transient colouration provided, for example, by a makeup pigment; and mixtures thereof.

Examples of self-tanning agents that may especially be mentioned include:
dihydroxyacetone (DHA),
erythrulose, and
the combination of a catalytic system formed from:
manganese and/or zinc salts and oxides, and
alkali metal and/or alkaline-earth metal hydrogen carbonates.

The self-tanning agents are generally chosen from mono-carbonyl or polycarbonyl compounds, for instance isatin, alloxan, ninhydrin, glyceraldehyde, mesotartaric aldehyde, glutaraldehyde, erythrulose, pyrazolin-4,5-dione derivatives as described in patent application FR 2 466 492 and WO 97/35842, dihydroxyacetone (DHA) and 4,4-dihydroxy-pyrazolin-5-one derivatives as described in patent application EP 903 342. DHA will preferably be used.

DHA may be used in free and/or encapsulated form, for example in lipid vesicles such as liposomes, described especially in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluorane type such as those described in patent application FR 2 840 806. Mention may be made, for example, of the following dyes:
tetrabromofluorescein or eosin known under the CTFA name: CI 45380 or Red 21
phloxin B known under the CTFA name: CI 45410 or Red 27
diiodofluorescein known under the CTFA name: CI 45425 or Orange 10;
dibromofluorescein known under the CTFA name: CI 45370 or Orange 5;
the sodium salt of tetrabromofluorescein known under the CTFA name: CI 45380 (Na salt) or Red 22;
the sodium salt of phloxin B known under the CTFA name: CI 45410 (Na salt) or Red 28;
the sodium salt of diiodofluorescein known under the CTFA name: CI 45425 (Na salt) or Orange 11;
erythrosine known under the CTFA name: CI 45430 or Acid Red 51;
phloxin known under the CTFA name: CI 45405 or Acid Red 98;

These dyes can also be chosen from anthraquinones, caramel, carmine, carbon black, azulene blues, methoxalene, trioxalene, guaiazulene, chamazulene, rose bengal, eosin 10B, cyanosine or daphinine.

These dyes may also be chosen from indole derivatives, for instance the monohydroxyindoles as described in patent FR 2 651 126 (i.e.: 4-, 5-, 6- or 7-hydroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihy-droxyindole).

The examples that follow serve to illustrate the invention without, however, being limiting in nature. In these examples, the amounts of the composition ingredients are given as weight percentages relative to the total weight of the composition.

EXAMPLES

Examples 1 to 7

The following compositions were prepared according to the procedure below:
In a beaker, phase B is heated to 80-85° C. until a homogeneous mixture is obtained.
Phase A is added to phase B with gentle stirring.
Phase C is added to phase A+B with gentle stirring.
the mixture is homogenized in a Rayneri deflocculator.

The macroscopic aspect is evaluated at 24 hours. The gloss after application of the compositions is evaluated using a MicroGloss 60° glossmeter from Byk-Gardner GmbH. A film of the composition 30 μm thick is drawn on an Erichsen Typ24/5 contrast card. After 24 hours of drying at 37° C., measurement of the gloss is performed using a glossmeter at an angle of 60°. The gloss value, expressed in Gloss Units, is given by the average of six measurements taken on the same contrast card.

| Phase | Ingredients | 1* | 2 |
|---|---|---|---|
| A | Dimethicone | 52.47 | 52.47 |
| B | Bis(ethylhexyloxyphenol)methoxyphenyltriazine | 1.34 | 1.34 |
|   | Drometrizole trisiloxane | 0.67 | 0.67 |
|   | Diethylaminohydroxybenzoylhexyl benzoate | 2.67 | 2.67 |
|   | Butylmethoxydibenzoylmethane | 4.01 | 4.01 |
|   | Ethylhexyl triazone | 2 | 2 |
|   | Ethylhexyl salicylate | 3.34 | 3.34 |
|   | Octocrylene | 6.68 | 6.68 |
|   | Diisopropyl sebacate | 16.02 | 16.02 |
|   | C12-15 Alkyl benzoate | 5.34 | 5.34 |
| C | Silica silylate (Aerogel VM2270 from Dow Corning) | 5.47 | — |
|   | Silica dimethyl silylate (Aerosil R972 from Evonik-Degussa) | — | 5.47 |

*composition according to the invention

Composition 2 outside the invention containing a phase containing at least one lipophilic UV-screening agent, a dimethicone and a standard filler (Aerosil R972 from Evonik-Degussa) is not homogeneous and undergoes phase separation. In contrast, composition 1 according to the invention is homogeneous and matt.

| Phase | Ingredients | 1* | 3 |
|---|---|---|---|
| A | Dimethicone | 52.47 | |
| B | Bis(ethylhexyloxyphenol)methoxyphenyltriazine | 1.34 | 1.34 |
|   | Drometrizole trisiloxane | 0.67 | 0.67 |
|   | Diethylaminohydroxybenzoylhexyl benzoate | 2.67 | 2.67 |
|   | Butylmethoxydibenzoylmethane | 4.01 | 4.01 |
|   | Ethylhexyl triazone | 2 | 2 |
|   | Ethylhexyl salicylate | 3.34 | 3.34 |
|   | Octocrylene | 6.68 | 6.68 |
|   | Diisopropyl sebacate | 16.02 | 16.02 |
|   | C12-15 Alkyl benzoate | 5.34 | 5.34 |
| C | Silica silylate (Aerogel VM2270 from Dow Corning) | 5.47 | — |
|   | Dimethicone (and) Dimethicone/Polyglycerin-3 Crosspolymer (KSG710 from Shin-Etsu) | — | 20 10 |
|   | Cyclopentasiloxane (and) Dimethicone Crosspolymer (DC9045 from Dow Corning) | — | 47.94 |

*composition according to the invention

Composition 3 containing an oil phase containing at least one lipophilic UV-screening agent, a non-emulsifying silicone elastomer, and an emulsifying silicone elastomer, according to patent application WO 2010/088 185, is not homogeneous and undergoes phase separation. Composition 1 according to the invention is homogeneous and matt.

| Ingredients | 1* | 4 | 5 | 6 |
|---|---|---|---|---|
| Dimethicone | 52.47 | — | — | — |
| Isohexadecane | — | 52.47 | — | — |
| Cyclohexasiloxane | — | — | 52.47 | — |
| C12-15 Alkyl benzoate | — | — | — | 52.47 |
| Bis(ethylhexyloxyphenol)methoxyphenyltriazine | 1.34 | 1.34 | 1.34 | 1.34 |
| Drometrizole trisiloxane | 0.67 | 0.67 | 0.67 | 0.67 |
| Diethylaminohydroxybenzoylhexyl benzoate | 2.67 | 2.67 | 2.67 | 2.67 |
| Butylmethoxydibenzoylmethane | 4.01 | 4.01 | 4.01 | 4.01 |
| Ethylhexyl triazone | 2 | 2 | 2 | 2 |
| Ethylhexyl salicylate | 3.34 | 3.34 | 3.34 | 3.34 |
| Octocrylene | 6.68 | 6.68 | 6.68 | 6.68 |
| Diisopropyl sebacate | 16.02 | 16.02 | 16.02 | 16.02 |
| C12-15 Alkyl benzoate | 5.34 | 5.34 | 5.34 | 5.34 |
| Silica silylate (Aerogel VM2270 from Dow Corning) | 5.47 | 5.47 | 5.47 | 5.47 |
| Gloss (glossmeter) | 3.9 ± 0.2 | 16.3 ± 3.9 | 7.3 ± 3.0 | 24.5 ± 4.2 |

*composition according to the invention

Compositions 4, 5 and 6 containing a silica aerogel and an oil phase containing at least one lipophilic UV-screening agent, but no dimethicone, are homogeneous, but are not matt, either in the jar or on application. Composition 1 according to the invention is homogeneous and matt in the jar. On application, it is significantly less glossy than the other compositions.

| Ingredients | 6* | 7* |
|---|---|---|
| Dimethicone | 51.85 | 51.17 |
| Bis(ethylhexyloxyphenol)methoxyphenyltriazine | 1.32 | 1.30 |
| Drometrizole trisiloxane | 0.66 | 0.65 |
| Diethylaminohydroxybenzoylhexyl benzoate | 2.64 | 2.60 |
| Butylmethoxydibenzoylmethane | 3.96 | 3.91 |
| Ethylhexyl triazone | 1.98 | 1.95 |
| Ethylhexyl salicylate | 3.3 | 3.26 |
| Octocrylene | 6.6 | 6.51 |
| Diisopropyl sebacate | 15.83 | 15.63 |
| C12-15 Alkyl benzoate | 5.28 | 5.21 |
| Silica silylate (Aerogel VM2270 from Dow Corning) | 6.6 | 7.81 |
| Gloss (glossmeter) | 3.2 ± 0.1 | 2.9 ± 0.3 |

*composition according to the invention

Compositions 6 and 7 according to the invention are homogeneous and matt, both in the jar and on application.

Examples 8 to 13

The following compositions were prepared according to the procedure below:
Phase $A_2$ is swollen in phase $A_1$ in a beaker under cold conditions with mixing using a Rayneri blender.
Phase $A_3$ is added to the mixture $A_1$-$A_2$. The mixture is homogenized using a Rayneri blender.
Phase $B_1$ is heated at 75° C. with magnetic stirring until it is homogeneous.
In another beaker, phase $B_2$ is added to phase $B_1$ and the mixture is homogenized by spatula until a homogeneous powder is obtained.
The mixture $B_1+B_2$ is added to the mixture $A_1+A_2+A_3$ with mixing using a Rayneri blender. The whole is homogenized.
Phase $C_1$ is added with mixing using a Rayneri blender. The whole is homogenized.
Phase $C_2$ is added with mixing using a Rayneri blender. The whole is homogenized.
The macroscopic aspect of the compositions is evaluated at 24 hours.
The gloss after application of the compositions is evaluated using a MicroGloss 60° glossmeter from Byk-Gardner GmbH. A film of the composition 30 μm thick is drawn on an Erichsen Typ24/5 contrast card. After 24 hours of drying at 37° C., measurement of the gloss is performed using a glossmeter at an angle of 60°. The gloss value, expressed in Gloss Units, is given by the average of six measurements taken on the same contrast card.

The sun protection factor (SPF) of the compositions is evaluated according to the International Method published by COLIPA/CTFA SA/JCIA (May 2006). The sun protection factor is the ratio of the Minimum Erythemal Dose obtained in the presence of product (2 mg/cm$^2$) (MEDp) to the Minimum Erythemal Dose obtained without product (MEDnp).

SPF=MEDp/MEDnp

The Minimum Erythemal Dose is defined as being the amount of energy necessary to produce the first unambiguous perceptible redness, with clearly defined contours, evaluated 16 to 24 hours after exposure to a sun simulator, at six increasing doses of UV (12% increments). The test must be performed on five individuals, and it must satisfy the statistical criterion (95% IC<17% SPF mean).

| Phase | Ingredients | 8* |
|---|---|---|
| $A_1$ | Dimethicone (5 cSt) | 39.3 |
| $A_2$ | Dimethicone (and) Dimethicone Crosspolymer (DC9041 from Dow Corning) | 2 |
| $A_3$ | Trimethyl siloxysilicate | 5 |
| $B_1$ | Bis(ethylhexyloxyphenol)methoxyphenyltriazine | 1 |
| | Drometrizole trisiloxane | 0.5 |
| | Diethylaminohydroxybenzoylhexyl benzoate | 2 |
| | Butylmethoxydibenzoylmethane | 3 |
| | Ethylhexyl triazone | 1.5 |
| | Ethylhexyl salicylate | 2.5 |
| | Octocrylene | 5 |
| | Diisopropyl sebacate | 12 |
| | C12-15 Alkyl benzoate | 4 |
| $B_2$ | Silica silylate (Aerogel VM2270 from Dow Corning) | 5 |
| $C_1$ | Talc | 6.7 |
| | Mica (and) bismuth oxychloride (and) carmine | 0.4 |
| | Mica (and) iron oxides | 0.1 |
| $C_2$ | Silica (and) titanium dioxide (Sunsil TIN 50 from Sunjin Chemical) | 10 |

*composition according to the invention

Composition 8 according to the invention is homogeneous and matt in appearance. It has a gloss, measured with a glossmeter, of less than 5. in vivo, it has a sun protection factor SPF of 51.3±0.4.8.

| Phase | Ingredients | 9* | 10* |
|---|---|---|---|
| $A_1$ | DIMETHICONE | 42.7 | 43 |
| $A_2$ | Dimethicone (and) dimethicone crosspolymer | 2 | 2 |
| $A_3$ | Trimethyl siloxysilicate | 5 | 5 |
| $B_1$ | Bis(ethylhexyloxyphenol)methoxyphenyltriazine | 1 | 1 |
| | Drometrizole trisiloxane | 0.5 | 0.5 |
| | Diethylaminohydroxybenzoylhexyl benzoate | 2 | 2 |
| | Butylmethoxydibenzoylmethane | 3 | 3 |
| | Ethylhexyl triazone | 1.5 | 1.5 |
| | Ethylhexyl salicylate | 2.5 | 2.5 |
| | Octocrylene | 5 | 5 |
| | Diisopropyl sebacate | 12 | 12 |
| | C12-15 Alkyl benzoate | 4 | 4 |
| $B_2$ | Silica Silylate | 5 | 5 |
| $C_1$ | Talc | 7.3 | 7.5 |
| | Mica (and) bismuth oxychloride (and) carmine | 0.4 | 0.4 |
| | Mica (and) iron oxides | 0.1 | 0.1 |
| $C_2$ | Titanium dioxide (and) silica (and) aluminum hydroxide (and) alginic acid (MT-100AQ from Tayca) | 6 | |
| | Titanium dioxide (and) silica (Eusolex T-AVO from Merck) | | 5.5 |

*composition according to the invention

Compositions 9 and 10 according to the invention are homogeneous and matt in appearance. They have a gloss, measured with a glossmeter, of less than 5. in vivo, they have a sun protection factor SPF of 46.9±2.9 for composition 9 and 48.9±2.4 for composition 10.

| Phase | Ingredients | 11* |
|---|---|---|
| $A_1$ | Dimethicone | 33.3 |
| $A_2$ | Dimethicone (and) dimethicone crosspolymer | 2 |
| $A_3$ | Trimethyl siloxysilicate | 5 |
| $B_1$ | Bis(ethylhexyloxyphenol)methoxyphenyltriazine | 1 |
| | Drometrizole trisiloxane | 0.5 |
| | Diethylaminohydroxybenzoylhexyl benzoate | 2 |
| | Butylmethoxydibenzoylmethane | 3 |
| | Ethylhexyl triazone | 1.5 |
| | Ethylhexyl salicylate | 2.5 |
| | Octocrylene | 5 |
| | Diisopropyl sebacate | 12 |
| | C12-15 Alkyl benzoate | 4 |
| $B_2$ | Silica Silylate | 5 |
| $C_1$ | Glycerol | 7 |
| | Talc | 5.7 |
| | Mica (and) bismuth oxychloride (and) carmine | 0.4 |
| | Mica (and) iron oxides | 0.1 |
| $C_2$ | Silica (and) titanium dioxide | 10 |

*composition according to the invention

Composition 11 was prepared according to the following procedure:

Phase $A_2$ is swollen in phase $A_1$ in a beaker under cold conditions with mixing using a Rayneri blender.

In another beaker, phase $B_1$ is heated at 75° C. with magnetic stirring, until it is homogeneous. The mixture is left to cool.

Phase $B_2$ is added to phase $B_1$ and the mixture is homogenized by spatula until a homogeneous powder is obtained.

The mixture $B_1+B_2$ is added to the mixture $A_1+A_2$ with mixing using a Rayneri blender. The whole is homogenized gently.

Composition 11 according to the invention is homogeneous and matt in appearance. It has a gloss, measured with a glossmeter, of less than 5. in vivo, it has a sun protection factor SPF of 46.9±2.8.

| Phase | Ingredients | 12* |
|---|---|---|
| $A_1$ | Dimethicone | 31.5 |
| | PEG-30 dipolyhydroxystearate | 3 |
| $A_2$ | Dimethicone (and) dimethicone crosspolymer | 2 |
| | Trimethyl siloxysilicate | 5 |
| B | Glycerol | 7 |
| | Water | 5 |
| $C_1$ | Bis(ethylhexyloxyphenol)methoxyphenyltriazine | 1 |
| | Drometrizole trisiloxane | 0.5 |
| | Diethylaminohydroxybenzoylhexyl benzoate | 2 |
| | Butylmethoxydibenzoylmethane | 3 |
| | Ethylhexyl triazone | 1.5 |
| | Ethylhexyl salicylate | 2.5 |
| | Octocrylene | 5 |
| | Diisopropyl sebacate | 12 |
| | C12-15 Alkyl benzoate | 4 |

-continued

| Phase | Ingredients | 12* |
|---|---|---|
| $C_2$ | Silica silylate (Aerogel VM2270 from Dow Corning) | 5 |
| $D_1$ | Talc | 6.5 |
| | Mica (and) bismuth oxychloride (and) carmine | 0.4 |
| | Mica (and) iron oxides | 0.1 |
| $D_2$ | Silica (and) titanium dioxide | 10 |

*composition according to the invention

Composition 12 was prepared according to the following procedure:
Phase $A_2$ is swollen in phase $A_1$ in a beaker under cold conditions with mixing using a Rayneri blender.
Phase $A_3$ is added to the mixture $A_1+A_2$ with mixing using a Rayneri blender. The whole is homogenized.
Phase B is emulsified in the mixture $A_1+A_2+A_3$, with mixing using a Rayneri blender.
In another beaker, phase $C_1$ is heated at 75° C. with magnetic stirring, until it is homogeneous.
Phase $C_2$ is added to phase $C_1$ and the mixture is homogenized by spatula until a homogeneous powder is obtained.
The mixture $C_1+C_2$ is added to the emulsion with mixing using a Rayneri blender. The whole is homogenized gently.
Phase $D_1$ is added with mixing using a Rayneri blender. The whole is homogenized gently.
Phase $D_2$ is added with mixing using a Rayneri blender. The whole is homogenized gently.
Composition 12 according to the invention is homogeneous and matt in appearance. It has a gloss, measured with a glossmeter, of less than 5.

| Phase | Ingredients | 13* |
|---|---|---|
| $A_1$ | Dimethicone | 79.8 |
| $A_2$ | Silica silylate (Aerogel VM2270 from Dow Corning) | 3.5 |
| $B_1$ | Butylmethoxydibenzoylmethane | 3 |
| | Ethylhexyl salicylate | 5 |
| | Octocrylene | 7 |
| $B_2$ | Silica silylate (Aerogel VM2270 from Dow Corning) | 1.7 |

*composition according to the invention

Composition 13 according to the invention is homogeneous and matt in appearance. It has a gloss, measured with a glossmeter, of less than 5. in vivo, it has an SPF of 15.3±2.2.

The invention claimed is:

1. A homogenous and matt composition comprising, in a cosmetically acceptable medium, at least one continuous oil phase, wherein the oil phase comprises
   a) 5 to 60% by weight based upon the weight of the composition of at least one non-cyclic silicone oil with a viscosity at 25° C. ranging from 4 to 5000 mm²/s and having a vapour pressure of less than $10^{-3}$ mmHg (0.13 Pa), wherein said non-cyclic silicone oil is a dimethicone represented by formula (II) below:

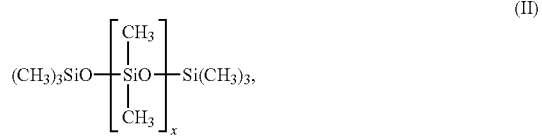

(II)

where x in formula (II) is an integer ranging from 1 to 50,
   b) 5% to 40% of at least one lipophilic organic UV-screening agent selected from the group consisting of butylmethoxydibenzoylmethane, octocrylene, ethylhexyl salicylate, n-hexyl 2-(4-diethylamino-2-hydroxybenzoyl)benzoate, bis(ethylhexyloxyphenyl)methoxyphenyltriazine, ethylhexyl triazone, diethylhexyl butamido triazone, drometrizole trisiloxane, and mixtures thereof; and
   c) hydrophobic silica aerogel particles with a specific surface area per unit of mass (SM) ranging from 600 to 1200 m²/g and a size, expressed as the volume mean diameter (D[0.5]), of 5 to 20 μm, wherein the amount of the hydrophobic silica aerogel particles is 0.5 to 10% by weight based upon the weight of the composition.

2. The composition according to claim 1, in the form of an anhydrous composition or a water-in-oil emulsion.

3. The composition according to claim 1, wherein the hydrophobic silica aerogel particles have a size, expressed as the volume mean diameter, ranging from 5 to 15 μm.

4. The composition according to claim 1, wherein the hydrophobic silica aerogel particles have a tamped density ρ ranging from 0.04 g/cm³ to 0.10 g/cm³.

5. The composition according to claim 1, wherein the hydrophobic silica aerogel particles have a specific surface area per unit volume SV ranging from 5 to 60 m²/cm³.

6. The composition according to claim 1, wherein the hydrophobic silica aerogel particles have an oil-absorbing capacity, measured at the wet point, ranging from 5 to 18 ml/g of particles.

7. The composition according to claim 1, wherein the hydrophobic silica aerogel particles are silica particles modified with trimethylsilyl groups.

8. The composition according to claim 1, also comprising at least one insoluble UV-screening agent selected from the group consisting of insoluble organic UV-screening agents, inorganic UV-screening agents and composite materials comprising an organic or inorganic matrix and at least one inorganic UV-screening agent.

9. The composition according to claim 1, also comprising an additional filler.

10. The composition according to claim 1, also comprising at least one colouring agent selected from the group consisting of pigments, nacres, water-soluble or liposoluble dyes, and agents for promoting the naturally pinkish colouration of the skin, and mixtures thereof.

11. The composition according to claim 1, in the form of a water-in-oil emulsion also comprising at least one hydrophilic UV-screening agent.

12. A cosmetic process for caring for and/or making up human keratin materials, especially bodily or facial skin or the hair, comprising at least the application to the surface of the keratin material of at least one composition as defined according to claim 1.

13. The composition according to claim 2, wherein the hydrophobic silica aerogel particles have a size, expressed as the volume mean diameter, ranging from 5 to 15 μm.

14. The composition according to claim 2, wherein the hydrophobic silica aerogel particles have a tamped density ρ ranging from 0.04 g/cm³ to 0.10 g/cm³.

15. The composition according to claim 3, wherein the hydrophobic silica aerogel particles have a tamped density ρ ranging from 0.04 g/cm³ to 0.10 g/cm³.

16. The composition according to claim 2, wherein the hydrophobic silica aerogel particles have a specific surface area per unit volume SV ranging from 5 to 60 m²/cm³.

17. The composition according to claim 3, wherein the hydrophobic silica aerogel particles have a specific surface area per unit volume SV ranging from 5 to 60 $m^2/cm^3$.

18. The composition according to claim 4, wherein the hydrophobic silica aerogel particles have a specific surface area per unit volume SV ranging from 5 to 60 $m^2/cm^3$.

19. The composition according to claim 1, wherein the amount of the hydrophobic silica aerogel particles is 1 to 10% by weight based upon the weight of the composition.

20. The composition according to claim 1, wherein x in formula (II) is an integer ranging from 1 to 20.

21. The composition according to claim 1, wherein x in formula (II) is an integer ranging from 1 to 10.

22. The composition according to claim 1, wherein the hydrophobic silica aerogel particles have a specific surface area per unit of mass (SM) ranging from 600 to 800 $m^2/g$.

23. The composition according to claim 22, wherein the hydrophobic silica aerogel particles have a size, expressed as the volume mean diameter (D[0.5]), of 5 to 15 μm.

* * * * *